United States Patent [19]

Collin et al.

[11] Patent Number: 4,697,029

[45] Date of Patent: Sep. 29, 1987

[54] PHOSPHOBROMINATED POLYETHERPOLYOLS AND PROCESSES FOR PRODUCTION THEREOF

[75] Inventors: André Collin, Ligny; Henri Wautier, Braine-le-Comte, both of Belgium

[73] Assignee: Solvay & Cie. (Société Anonyme), Brussels, Belgium

[21] Appl. No.: 821,021

[22] Filed: Jan. 17, 1986

[30] Foreign Application Priority Data

Jan. 24, 1985 [FR] France ............................ 85 01109

[51] Int. Cl.$^4$ ........................... C07F 9/09; C07F 9/40
[52] U.S. Cl. ..................................... 558/92; 521/169; 558/98; 558/165; 558/186
[58] Field of Search ............... 558/165, 186, 92, 99

[56] References Cited

U.S. PATENT DOCUMENTS

| | | | |
|---|---|---|---|
| 3,294,873 | 12/1966 | Lutz et al. | 558/165 |
| 4,044,074 | 8/1977 | Walsh et al. | 558/165 |
| 4,180,532 | 12/1979 | Chakrabarti et al. | 558/165 |
| 4,220,611 | 9/1980 | Wolf | 558/165 |
| 4,298,709 | 11/1981 | Ginter et al. | 521/169 |

FOREIGN PATENT DOCUMENTS 2539982  4/1976  Fed. Rep. of Germany.

Primary Examiner—Anton H. Sutto
Attorney, Agent, or Firm—Spencer & Frank

[57] ABSTRACT

Phosphobrominated polyetherpolyols which contain in their molecule oxyalkylene radicals bound to phosphorus atoms in the phosphate or phosphonate state and 1,4-dioxy-2,3-dibromo-2-butylene radicals in which the ratio of the total number of oxyalkylene radicals to the total number of phosphorus atoms is equal to at least 7.

These polyetherpolyols can be used as flame-retarding reactive additives in the manufacture of flame-retardant flexible polyurethane foams involving polyetherpolyols, the foams possessing good comfort-conferring properties.

7 Claims, No Drawings

PHOSPHOBROMINATED POLYETHERPOLYOLS AND PROCESSES FOR PRODUCTION THEREOF

The present invention relates to new phosphobrominated polyetherpolyols, processes for production of these polyetherpolyols and the use of these polyetherpolyols in the manufacture of flame-retardant flexible polyurethane foams.

By virtue of their comfort-conferring properties, flexible polyurethane foams find a multiplicity and variety of applications in industry, and in particular in the household furniture, quilting and upholstery padding sectors, in which fire resistance is, moreover, a desirable or even an essential property.

There are many means for imparting fire-resistance properties to polyurethane foams. A well-known process consists in incorporating unreactive flame-retardant additives, such as unreactive halogenated and/or phosphorus-containing organic compounds, in the polyetherpolyols intended for the manufacture of polyurethane foams. These additives, which are not chemically bound to the base polymer, are incapable of providing for permanent and uniformly distributed fire resistance.

Another known means consists in employing halogenated and/or phosphorus-containing polyetherpolyols which provide for permanent fire resistance in the resulting polyurethane foams.

However, it has now been found that a significant number of phosphohalogenated polyetherpolyols which can be used to render polyetherpolyol-based flexible polyurethane foams permanently flame-retardant possess serious disadvantages, such as instability to hydrolysis and/or deterioration of the comfort-conferring properties and more especially of the load-bearing capacity (compressive strength) of the resulting polyurethane foams.

The object of the present invention, as the latter is characterized in the claims, is to provide a new class of phosphobrominated polyetherpolyols which contain in their molecule oxyalkylene radicals bound to phosphorus atoms in the phosphate or phosphonate state and 1,4-dioxy-2,3-dibromo-2-butylene radicals, and which can be used in the manufacture of flame-retardant flexible polyurethane foams which do not possess the abovementioned disadvantages.

The preferred phosphobrominated polyetherpolyols according to the invention correspond to the general formula (I):

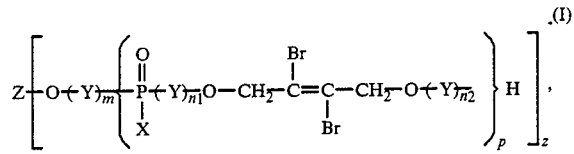

in which:

Z denotes a non-hydroxylated aliphatic radical containing from 1 to 6 carbon atoms and of valence z Y denotes oxyalkylene radicals derived from ethylene oxide, propylene oxide and/or butylene oxide, the radicals Y derived from ethylene oxide representing at most 50 moles % of all the Y radicals X denotes monovalent aliphatic radicals, which may be identical or different, chosen from radicals of the —R or —OR type in which R denotes a saturated alkyl radical, optionally halogenated, containing from 1 to 3 carbon atoms, and radicals of the type

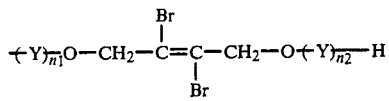

$z$ denotes an integer ranging from 1 to 4
$m$ denotes a number such that $0 \leq zm \leq 50\,z$
$p$ denotes a number such that $z \leq zp \leq 5\,z$ and
$n_1$ and $n_2$ denote numbers other than zero, such that $2\,pz \leq pz(n_1+n_2) \leq 12\,pz$, these phosphobrominated polyetherpolyols being further characterized by a ratio of the total number of oxyalkylene radicals to the total number of phosphorus atoms equal to at least 7.

The phosphobrominated polyetherpolyols according to the invention which result from successive condensation reactions do not correspond to well-defined chemical formulae. For this reason, the general formula (I) has to be established statistically. In this formula, the aliphatic radical Z corresponds to the non-hydroxylated residue of the hydroxylated initiator of general formula:

$$Z\text{-}(\text{O-}(Y)_{\overline{m}}\text{-H})_z \qquad (II)$$

used for manufacturing the phosphobrominated polyetherpolyols according to the invention, the oxyalkylene radicals $(Y)_m$ correspond, without discrimination to the formulae

and the radicals $(Y)_n$ (where $n = n_1$ or $n_2$) correspond, without discrimination, to the formulae

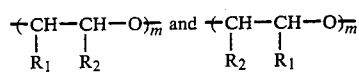

in which the radicals $R_1$ and $R_2$ denote, independently of each other and depending on the alkene oxide used, hydrogen, a methyl group or an ethyl group.

The hydroxylated initiator (II) can be chosen without discrimination from saturated or unsaturated monomeric aliphatic alcohols and polyols which are optionally halogenated and which contain from 1 to 6 carbon atoms and from 1 to 4 hydroxyl groups ($z = 1$ to 4) (in the case where $mz = 0$) and the products of addition of $mz$ moles of ethylene oxide, propylene oxide and/or butylene oxide to the abovementioned monomeric aliphatic alcohols and polyols (in the case where $mz \neq 0$).

By way of non-limitative examples of such initiator monomeric aliphatic alcohols and polyols of general formula (II) in which $mz = 0$, there may be mentioned $C_1$ to $C_6$ alcohols, ethylene glycol, propylene glycol and hexamethylene glycol, glycerol, butane- and hexanetriols, trimethylolpropane, pentaerythritol, diethylene glycol, triethylene glycol, glycerol monochloro- and monobromohydrins, 3,4-dibromo-1,2-butanediol, 2,3-dibromo-1,4-butanediol, 2,3-dibromo-2-butene-1,4-diol, 2,2-bis(bromomethyl)-1,3-propanediol and 1,2,5,6-tetrabromo-3,4-hexanediol.

By way of non-limitative examples of hydroxylated initiators of general formula (II) in which mz is other than zero, there may be mentioned the products of addition of ethylene oxide, propylene oxide and/or butylene oxide with the abovementioned monomeric aliphatic alcohols and polyols. Nevertheless, preference is given to monomeric aliphatic polyols containing from 3 to 5 carbon atoms and 2 or 3 hydroxyl groups. Most especially preferred initiator monomeric polyols are glycerol, 2,3-dibromo-2-butene-1,4-diol and 2,2-bis(-bromomethyl)-1,3-propanediol.

The resulting polyoxyalkylenepolyols are wellknown products which are advantageously manufactured by oligomerization of an alkene oxide or a mixture of alkene oxides with an initiator monomeric alcohol or polyol. Preference is given to propylene oxide and butylene oxide and to mixtures of propylene oxide or butylene oxide with ethylene oxide containing at most 50 moles % of ethylene oxide. According to an especially preferred embodiment of the invention, all the radicals $(Y)_m$ are derived from propylene oxide.

The hydroxylated initiator (II) is consequently preferably chosen from initiators of general formula

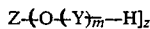

$$Z\text{-}[O\text{-}(Y)_{\overline{m}}\text{-}H]_z \qquad (II)$$

in which:
Z denotes a non-hydroxylated radical containing from 3 to 5 carbon atoms and of valence z
Y denotes oxyalkylene radicals derived from propylene oxide
z denotes an integer ranging from 2 to 3
m denotes a number such that $z \leq zm \leq 25 z$.

The preferred phosphobrominated polyetherpolyols are consequently those of general formula (I) in which Z, Y, z and m correspond to the abovementioned specifications.

Most especially preferred phosphobrominated polyetherpolypols are those defined above in which Z denotes a non-hydroxylated radical chosen from the radicals derived from glycerol, 2,3-dibromo-2-butene-1,4-diol and 2,2-bis(bromomethyl)-1,3-propanediol.

In the general formula (I), the radicals

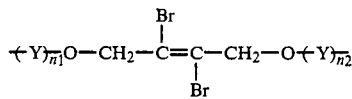

originate from the condensation reaction between a chlorine atom of a phosphochlorinated reagent and a brominated polyoxyalkylenediol of general formula

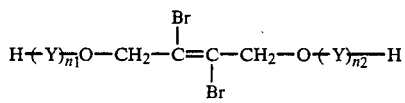

The brominated polyoxyalkylenediols (III) are also well-known products which are advantageously manufactured by oligomerization of ($n_1+n_2$) moles of an alkene oxide with one mole of 2,3-dibromo-2-butene-1,4-diol or alternatively with one mole of 2-butylene-1,4-diol followed by partial additive bromination of the acetylenic unsaturation.

The brominated polyoxyalkylenediol is preferably chosen from those of general formula (III) in which:

Y denotes oxyalkylene radicals derived from propylene oxide and $n_1$ and $n_2$ denote numbers other than zero such that $2 pz \leq pz (n_1+n_2) \leq 10 pz$.

Preferred phosphobrominated polyetherpolyols are consequently those of general formula (I) in which Y and
$n_1$ and $n_2$ correspond to the abovementioned specifications.

Preference is given, moreover, to the phosphobrominated polyetherpolyols of general formula (I) in which:
p denotes a number such that $z \leq zp \leq 3 z$, that is to say containing an average from 1 to 3 phosphorus atoms per hydroxyl group of the hydroxylated initiator (II).

As regards the radicals X in the general formula (I), these originate, according to a first embodiment of the invention, from the radicals X of the phosphodichlorinated reagent or reagents used when the latter are chosen from the products corresponding to the general formula

in which
X denotes monovalent aliphatic radicals, which may be identical or different, of the —R or —OR type in which R denotes a saturated alkyl radical, optionally halogenated, containing from 1 to 3 carbon atoms.

According to a second embodiment of the invention, the radicals X in the general formula (I) originate from condensation reactions between chlorine atoms of the phosphotrichlorinated reagent and a saturated aliphatic alcohol, optionally halogenated, containing from 1 to 3 carbon atoms and/or a brominated polyoxylkylenediol of general formula (III).

Preference is given to the phosphobrominated polyetherpolyols of general formula (I) in which:
X denotes monovalent aliphatic radicals, which may be identical or different, chosen from radicals of the —OR type in which
R denotes a halogenated aliphatic radical containing 2 or 3 carbon atoms, the halogen being chosen from chlorine and bromine, and radicals of the type

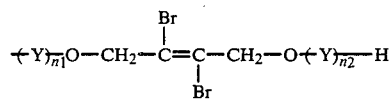

Phosphobrominated polyetherpolyols according to the invention which are especially preferred are consequently those which correspond to the general formula (I)
in which:
Z denotes a non-hydroxylated aliphatic radical containing from 3 to 5 carbon atoms and of valence z
Y denotes oxyalkylene radicals derived from propylene oxide
X denotes monovalent aliphatic radicals, which may be identical or different, chosen from radicals of the —OR type in which R denotes a halogenated aliphatic radical containing 2 or 3 carbon atoms, the halogen being chosen from chlorine and bromine, and radicals of the type

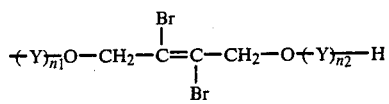

z denotes an integer ranging from 2 to 3
m denotes a number such that $z \leq zm \leq 25\,z$
p denotes a number such that $z \leq zp \leq 3\,z$ and
$n_1$ and $n_2$ denote numbers other than zero such that $2\,pz \leq pz\,(n_1+n_2) \leq 10\,pz$.

Phosphobrominated polyetherpolyols according to the invention in which, moreover, preference is given are those characterized by a ratio of the total number of oxyalkylene radicals to the total number of phosphorus atoms of between 8 and 12.

By means of a simple calculation, three examples of which are given in detail below to enable the invention to be more clearly understood, it is possible to work out the minimum mean values which it will be appropriate to choose for the parameters m, $n_1$ and $n_2$, and p in order to comply with the critical ratio of the total number of oxyalkylene radicals to the total number of phosphorus atoms in the phosphobrominated polyetherpolyols according to the invention.

First calculation example

Let it be assumed that the parameter p is set equal to 1, the addition product of 12 moles of propylene oxide with one mole of glycerol (zm=12; z=3) is chosen as hydroxylated initiator (III) and radicals X are chosen to be equal to —R or —OR. The resulting phosphobrominated polyetherpolyol will possess a functionality equal to 3 and will contain pz, equivalent to 3 phosphorus atoms.

In this case, the minimum value of $(n_1+n_2)$ to be complied with is calculated as follows:

$$\frac{12 + 3\,(n_1 + n_2)}{3} \geq 7,$$

whence $(n_1+n_2) \geq 3$.

In this instance, the choice will consequently be made of a brominated polyoxyalkylenediol (III) resulting from the addition of, on average, at least 3 moles of alkene oxide to one mole of 2,3-dibromo-2-butene-1,4-diol.

Second calculation example

Let it be assumed that the parameters z and p are set equal to 2, the addition product of 4 moles of propylene oxide with one mole of 2,3-dibromo-2-butene-1,4-diol is chosen as brominated polyoxyalkylenediol (III) and radicals X are chosen to be equal to —R or —OR. The resulting phosphobrominated polyetherpolyol will possess a functionality equal to 2 and will contain 4 phosphorus atoms.

In this case, the minimum value of m is calculated as follows:

$$\frac{(2 \times 2 \times 4) + 2\,m}{4} \geq 7,$$

whence $m \geq 6$

In this distance, the choice will consequently be made of a hydroxylated initiator (II) resulting from the addition of, an average, at least 12 moles of alkene oxide to one mole of aliphatic diol.

Third calculation example

Let it be assumed that the parameter p is set equal to 1, the product of the reaction of 4 moles of propylene oxide with one mole of 2,2-bis(bromomethyl)-1,3-propanediol (zm=4; z=2) is chosen as hydroxylated initiator (II) and a radical —R and a radical derived from brominated polyoxyalkylenediol (III) are chosen as radicals X. The resulting phosphobrominated polyetherpolyol will contain 2 phosphorus atoms and 2 radicals X, only one of which will derive from brominated polyoxyalkylenediol (III).

In this case, the minimum value of $(n_1+n_2)$ is calculated as follows:

$$\frac{4 + 2\,(n_1 + n_2) + 1\,(n_1 + n_2)}{2} \geq 7,$$

whence $(n_1+n_2) \geq 3.33$

In this instance, the choice will consequently be made of a brominated polyoxyalkylenediol (III) resulting from the addition of, an average, at least 3.33 moles of alkene oxide to one mole of 2,3-dibromo-2-butene-1,4-diol.

The present invention also aims to provide processes for producing the phosphobrominated polyetherpolyols according to the invention.

According to a first method of production, there is employed a phosphodichlorinated reagent of general formula

in which:
X denotes monovalent aliphatic radicals chosen from —R or —OR radicals in which R denotes a saturated alkyl radical, optionally halogenated, containing from 1 to 3 carbon atoms (dichlorophosphates and phosphonic dichlorides). In this case, the process for producing phosphobrominated polyetherpolyols according to the invention comprises two stages.

A first method of producing phosphobrominated polyetherpolyols according to the invention therefore consists,
in a first stage, in condensing z moles of phosphodichlorinated reagent (IV) in the presence of one mole of hydroxylated initiator (II) to produce a phosphochlorinated product of general formula:

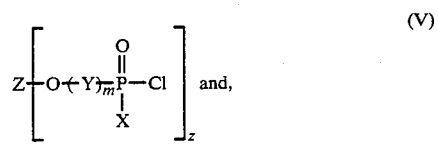

in a second stage, in condensing in the presence of the product (V) resulting from the preceding stage pz moles of brominated polyoxyalkylenediol (III) and (p−1) z moles of phosphodichlorinated reagent (IV).

According to a second method of production, the phosphochlorinated reagent is phosphorus oxychloride (POCl$_3$). In this case, the process for producing phosphobrominated polyetherpolyols according to the invention comprises three stages.

A second method of producing phosphobrominated polyetherpolyols according to the invention therefore consists,
in a first stage, in condensing z moles of phosphorus oxychloride in the presence of one mole of hydroxylated initiator (II) to produce a phosphodichlorinated product of general formula:

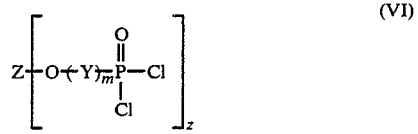
(VI)

in a second stage, in condensing in the presence of the product (VI) of the preceding stage pz moles of brominated polyoxyalkylenediol (III) and (p−1) z moles of phosphorus oxychloride to produce a phosphobrominated polyetherpolyol of general formula:

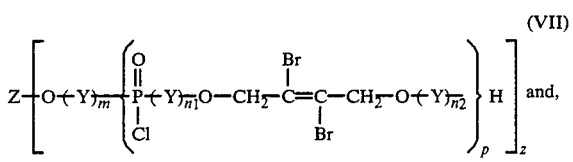 and, (VII)

in a third stage, in condensing in the presence of the product (VII) resulting from the preceding stage a total of pz moles of saturated aliphatic alcohol, optionally halogenated, containing from 1 to 3 carbon atoms and/or brominated polyoxyalkylenediol (III).

Preference is given to the production process involving phosphorus oxychloride, since it enables the mean functionality of the phosphobrominated polyetherpolyols according to the invention to be adjusted "in situ".

The production processes according to the two variants described above are performed at low temperature, as a general rule at between 0° and 25° C. approximately, in organic solvents such as common aromatic or chlorinated solvents of the benzene, toluene, methylene chloride, tetrachloromethane or 1,2-dichloroethane type. A chlorinated solvent is preferably used, and still more especially 1,2-dichloroethane.

The condensation reactions, which all proceed through elimination of hydrochloric acid, are greatly accelerated by the presence of organic or inorganic basic compounds. Preference is nevertheless given to organic basic compounds, the best results having been obtained with tertiary amines such as triethylamine and pyridine.

The latter constitutes a most especially preferred basic accelerator.

An especially advantageous embodiment, moreover, consists in introducing all the phosphochlorinated reagent at the beginning of the production processes according to one or other of the two variants, and in regulating the progress of the successive condensation reactions by the successive addition of suitable amounts of basic accelerator. It is preferable to employ a slight excess, from 1 to 5 moles % approximately, of basic accelerator relative to the stoichiometric amounts.

The addition of a tertiary amine to the reaction mixture brings about the elimination of hydrochloric acid in the form of amine hydrochloride, which can then be removed from the reaction mixture by any known means, such as filtration or washing with water.

The phosphobrominated polyetherpolyols according to the invention can be recovered from the reaction mixture by any suitable operation which is known for this purpose. A satisfactory manner consists in evaporating the organic solvent at a moderate temperature and under reduced pressure.

A preferred embodiment of the processes for producing phosphobrominated polyetherpolyols according to the invention consequently consists in carrying out the different condensation stages in a chlorinated organic solvent at low temperature in the presence of an organic basic accelerator chosen from tertiary amines, preferably pyridine, and, moreover, in introducing all the phosphochlorinated reagent at the beginning of the first stage, the progress of the successive condensation stages being regulated by the successive addition of suitable amounts of basic accelerator.

The phosphobrominated polyetherpolyols according to the invention are liquids of low viscosity, possessing a dynamic viscosity measured according to DIN standard 530K of September 1978 of less than 30 Pa.s, and generally between 5 and 15 Pa.s. They possess a hydroxyl number generally between 20 and 70 mg KOH/g of phosphobrominated polyetherpolyol, an acid number generally less than 5 mg KOH/g of phosphobrominated polyetherpolyol, a phosphorus content of approximately 2 to 5% by weight and a bromine content of approximately 10 to 25% by weight. The phosphobrominated polyetherpolyols according to the invention are, moreover, miscible in all proportions with the polyetherpolyols which are conventional for flexible polyurethane foams based mainly on propylene oxide.

The phosphobrominated polyetherpolyols according to the invention can be used as flame-retarding reactive additives for polyetherpolyols intended for the manufacture of flexible polyurethane foams.

A surprising aspect of the phosphobrominated polyetherpolyols according to the invention resides precisely in the fact that, when used as flame-retarding reactive additives for conventional non-halogenated polyetherpolyols, the compounds of the invention do not have an adverse effect on the comfort-conferring properties, and in particular the load-bearing capacity, of the resulting foams.

The present invention also relates to the use of the phosphobrominated polyetherpolyols according to the invention as flame-retarding reactive additives in the manufacture of flame-retardant flexible polyurethane foams involving polyetherpolyols.

According to a preferred embodiment of the invention, phosphobrominated polyetherpolyols according to any one of claims 2 or 4 are used as flame-retarding reactive additives in the manufacture of flame-retardant flexible polyurethane foams involving polyetherpolyols based mainly on propylene oxide.

The amount of phosphobrominated polyetherpolyol to be used is not especially critical, and the minimum amounts needed to provide for the self-extinguishing properties of the resulting polyurethane foam depend, inter alia, on the density of the latter. As a guide, the phosphobrominated polyetherpolyols according to the invention are generally used in the proportion of 2 to 50% by weight, and still more especially in the proportion of 2 to 30% by weight, of the mixture of polyetherpolyols intended for the manufacture of flame-retardant flexible polyurethane foams.

In other respects, the general conditions for manufacturing flame-retardant flexible polyurethane foams involving mixtures of phosphobrominated polyetherpolyols according to the invention and polyetherpolyols are those which are usually employed for the manufacture of polyetherpolyol-based flexible polyurethane foams and which, are moreover, well known to those versed in the art.

The examples which follow illustrate the invention without, however, limiting it.

Examples 1 to 4 illustrate the production of phosphobrominated polyetherpolyols according to the invention. Comparative Example 5 illustrates the production of phosphobrominated polyetherpolyols outside the scope of the invention.

Examples 6 to 10 illustrate the production of flexible polyurethane foams involving polyetherpolyols. In Examples 6 and 7, phosphobrominated polyetherpolyols according to the invention produced in Examples 2 and 1, respectively, are employed. In Comparative Example 8, phosphobrominated polyetherpolyols outside the scope of the invention obtained in Comparative Example 5 are employed. In Comparative Example 9, a phosphochlorinated polyetherpolyol marketed by HOECHST under the name EXOLIT 413 is employed, and finally in Example 10, which is also comparative, a non-halogenated polyetherpolyol is exclusively employed.

The non-halogenated polyetherpolyol used mixed with phosphohalogenated polyetherpolyols in Examples 6 to 9, and used to the extent of 100% in Example 10, is a polyetherpolyol based on propylene oxide and ethylene oxide, having a molecular weight of 3,500 and a hydroxyl number of 48 mg KOH/g, marketed by CARBOHIMIQUE under the name TERCAROL 908.

EXAMPLE 1

Example 1 illustrates the production of pnospnobrominated polyetherpolyols of general formula (I) in which:

$$Z = -CH_2-CH-CH_2- \quad \text{and/or} \quad -CH-CH_2-O-$$
$$\qquad\qquad\quad | \qquad\qquad\qquad\qquad\qquad\quad |$$
$$\qquad\qquad\qquad\qquad\qquad\qquad\qquad\qquad\quad CH_3$$

$$Y = -CH_2-CH-O-$$
$$\qquad\qquad\quad |$$
$$\qquad\qquad\quad CH_3$$

$$X = -O-CH-CH_2Cl$$
$$\qquad\qquad\quad |$$
$$\qquad\qquad\quad CH_3$$

$z = 3$      $pz = 3$
$mz = 24.3$      $pz(n_1 + n_2) = 7.5$ and which possess a ratio of the total number of oxyalkylene groups to the total number of phosphorus atoms $$\frac{\Sigma Y}{\Sigma P} \text{ equal to } \frac{24.3 + 7.5}{3} = 10.6.$$

These polyetherpolyols are manufactured using a hydroxylated initiator (II) consisting of a polyoxypropylenetriol resulting from the addition of 24.3 moles of propylene oxide on average to one mole of glycerol, a brominated polyoxypropylenediol (III) resulting from the addition 2.5 moles of propylene oxide on average to one mole of 2,3-dibromo-2-butene-1,4-diol, phosphorus oxychloride (POCL$_3$) and 1-chloro-2-propanol.

(1) In a thermostatically controlled 2-liter reactor equipped with a stirrer, a reflux condenser, a dropping funnel and a dipping tube fed with pure, dry nitrogen, 624 g of 1,2-dichloroethane and 150 g (0.1 mole) of hydroxylated initiator (II), are introduced successively under an atmosphere of nitrogen. The mixture is brought to 0° C. with efficient stirring, continuous bubbling with nitrogen being maintained. 46 g (0.3 mole) of POCL$_3$ are then added rapidly. While the temperature of the reaction medium is maintained at 0° C., 23.7 g (0.3 mole) of pyridine are introduced in the course of 30 minutes by way of the dropping funnel. After introduction of the pyridine, the temperature of the reaction medium is brought to 20° C. and the reaction is allowed to continue at this temperature for 2 hours.

(2) After this time has elapsed, and still at 20° C., 117.3 g (0.3 mole) of brominated polyoxypropylenediol (III) are added rapidly, followed in the course of 30 minutes by 23.7 g (0.3 mole) of pyridine. After the reaction has proceeded for a further 3 hours at 20° C., there are added (3) 31.2 g (0.33 mole) of 1-chloro-2-propanol, followed in the course of 30 minutes by 24.9 g (0.315 mole) of pyridine. After the reaction has proceeded for 5 hours at 20° C., the pyridine hydrochloride formed, which precipitates during successive condensation reactions, is removed by means of washes with water. After removal of the volatile materials by evaporation at 80° C. under reduced pressure, 303 g (98% yield) are produced of a pale brown liquid corresponding to the phosphobrominated polyetherpolyols defined above, possessing the following characteristics:

|  | Theoretical values | Measured values |
|---|---|---|
| Molecular weight | ±3,000 |  |
| Bromine content, % by weight | 16 | 15.2 |
| Chlorine content, % by weight | 3.6 | 3.8 |
| Phosphorus content, % by weight | 3.1 | 3.3 |
| Hydroxyl number, mg KOH/g | 56 | 56 |
| Acid number, mg KOH/g | — | <0.3 |
| Mean functionality | 3 |  |
| Viscosity at 25° C., Pa.s | — | 10.7 |
| Specific gravity, g/cm$^3$ | — | 1.26 |

EXAMPLE 2

Example 2 illustrates the production of phosphobrominated polyetherpolyols of general formula (I) in which:

$$Z = -CH_2-\underset{\underset{Br}{|}}{\overset{\overset{Br}{|}}{C}}=C-CH_2-$$

$$Y = -CH_2-CH-O- \quad \text{and/or} \quad -CH-CH_2-O-$$
$$\qquad\qquad\quad | \qquad\qquad\qquad\qquad\qquad\qquad\quad |$$
$$\qquad\qquad\quad CH_3 \qquad\qquad\qquad\qquad\qquad\quad CH_3$$

-continued

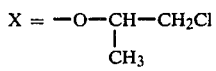

$$X = -O-CH-CH_2Cl$$
$$\phantom{X = -O-}|$$
$$\phantom{X = -O-}CH_3$$

$z = 2$      $pz = 2.3$
$mz = 6.5$      $pz (n_1 + n_2) = 14.95$ and which possess a ratio $$\frac{\Sigma Y}{\Sigma P} \text{equal to } \frac{6.5 + 14.95}{2.3} = 9.33.$$

These polyetherpolyols are manufactured using a hydroxylated initiator (II) and a brominated polyoxypropylenediol (III) which are identical and which both result from the addition of 6.5 moles of propylene oxide on average to one mole of 2,3-dibromo-2-butene-1,4-diol, phosphorus oxychloride (POCL$_3$) and 1-chloro-2-propanol.

Using the apparatus of Example 1 and under the general conditions of Example 1, the following are reacted in solution in 1,2-dichloroethane in three successive stages:

(1) 62.3 g (0.1 mole) of brominated polyoxypropylenediol (III) with 35.3 g (0.23 mole) of POCl$_3$ in the presence of 15.8 g (0.2 mole) of pyridine, (2) 143.3 g (0.23 mole) of brominated polyoxypropylenediol (III) are reacted with the product of the reaction (I) in the presence of 20.6 g (0.26 mole) of pyridine, (3) 24 g (0.25 mole) of 1-chloro-2-propanol are reacted with the product of the reaction (2) in the presence of 19.1 g (0.24 mole) of pyridine.

After the mixture is washed with water and the volatile materials are removed, a 98% yield is produced of the phosphobrominated polyetherpolyols as defined above, possessing the following characteristics:

|  | Theoretical values | Measured values |
|---|---|---|
| Molecular weight | ±2,400 |  |
| Bromine content, % by weight | 22.2 | 21.2 |
| Chlorine content, % by weight | 3.4 | 3.6 |
| Phosphorus content, % by weight | 3.0 | 3.2 |
| Hydroxyl number, mg KOH/g | 47 | 47 |
| Acid number, mg KOG/g | — | <0.3 |
| Mean functionality | 2 |  |
| Viscosity at 25° C., Pa.s | — | 12.4 |
| Specific gravity, g/cm$^3$ | — | 1.29 |

Identical phosphobrominated polyetherpolyols are produced by repeating Example 2 in two stages, with all the reagents used in the stages (1) and (2) introduced at the start of the reaction, the third stage of Example 1 then constituting the second stage.

EXAMPLE 3

Example 3 illustrates the production of phosphobrominated polyetherpolyols of general formula (I) in which

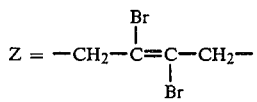

$$Z = -CH_2-C=C-CH_2-$$
with Br substituents

$$Y = -CH_2-CH-O- \quad \text{and/or} \quad -CH-CH_2-O-$$
$$\phantom{Y = -CH_2-}|\phantom{CH-O- \text{and/or} -CH-CH_2-}|$$
$$\phantom{Y = -CH_2-}CH_3 \phantom{-O- \text{and/or} -CH-CH_2-}CH_3$$

$$X = -O-CH_2-CH_3$$

and

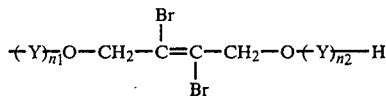

$$(Y)_{\overline{n_1}}O-CH_2-C=C-CH_2-O(Y)_{\overline{n_2}}H$$
with Br substituents (3 radicals X of the type —O—CH$_2$—CH$_3$ and 1 radical X of the dibrominated radical type)

$z = 2$      $pz = 4$
$mz = 6$      $pz (n_1 + n_2) = 24$ and which possess a ratio $$\frac{\Sigma Y}{\Sigma P} \text{equal to } \frac{6 + 24 + 6}{4} = 9$$

These polyetherpolyols are manufactured using a hydroxylated initiator (II) and a brominated polyoxypropylenediol (III) which are identical and which both result from the addition of 6 moles of propylene oxide on average to one mole of 2,3-dibromo-2-butene-1,4-diol, phosphorus oxychloride and ethanol.

Using the apparatus of Example 1, and under the general conditions of Example 1, the following are reacted in solution in 1,2-dichloroethane in three successive stages:

(1) 59.4 g (0.1 mole) of brominated polyoxypropylenediol (III) with 61.4 g (0.4 mole) of POCl$_3$ in the presence of 15.8 g (0.2 mole) of pyridine, (2) 297 g (0.5 mole) of brominated polyoxypropylenediol (III) are reacted with the product of the reaction (I) in the presence of 55.4 g (0.7 mole) of pyridine, (3) 15.2 g (0.33 mole) of ethanol are reacted with the product of the reaction (2) in the presence of 24.5 g of pyridine.

After the mixture is washed with water and the volatile materials are removed, a 98% yield is produced of the phosphobrominated polyetherpolyols as defined above, possessing the following characteristics:

|  | Theoretical values | Measured values |
|---|---|---|
| Molecular weight | ±3,900 |  |
| Bromine content, % by weight | 25 | 23.5 |
| Phosphorus content, % by weight | 3.2 | 3.4 |
| Hydroxyl number, mg KOH/g | 43 | 45 |
| Acid number, mg KOH/g | — | <0.3 |
| Mean functionality | 3 |  |
| Viscosity at 25° C., Pa.s | — | 4.4 |
| Specific gravity, g/cm$^3$ | — | 1.31 |

EXAMPLE 4

Example 4 illustrates the production of phosphobrominated polyetherpolyols of general formula (I) in which:

$$Z = -CH_2-\underset{\underset{Br}{|}}{\overset{\overset{Br}{|}}{C}}=C-CH_2-$$

$$Y = -CH_2-\underset{\underset{CH_3}{|}}{CH}-O- \quad \text{and/or} \quad -\underset{\underset{CH_3}{|}}{CH}-CH_2-O-$$

X = —O—CH$_2$—CH$_3$
z = 2             pz = 3
mz = 6.50         pz (n$_1$ + n$_2$) = 19.5 and which possess a ratio $$\frac{\Sigma Y}{\Sigma P}\text{equal to } \frac{6.5 + 19.50}{3} = 8.67.$$

These polyetherpolyols are manufactured using a hydroxylated initiator (II) and a brominated polyoxypropylenediol (III) which are identical and which both result from the addition of 6.5 moles of propylene oxide on average to one mole of 2,3-dibromo-2-butene-1,4-diol and ethyl dichlorophosphate (C$_2$H$_5$OPOCL$_2$).

Using the apparatus of Example 1 and under the general conditions of Example 1, the following are reacted in solution in dichloroethane in two successive stages:

(1) 62.3 g (0.1 mole) of brominated polyoxypropylenediol (III) with 48.9 g (0.3 mole) of ethyl dichlorophosphate in the presence of 15.8 g (0.2 mole) of pyridine, (2) 186.9 g (0.3 mole) of brominated polyoxypropylenediol (III) are reacted with the product of the reaction (1) in the presence of 34 g (0.43 mole) of pyridine.

After the mixture is washed with water and the volatile materials are removed, a 98% yield is produced of the phosphobrominated polyetherpolyols as defined above, possessing the following characteristics:

|  | Theoretical values | Measured values |
| --- | --- | --- |
| Molecular weight | ±2,750 | |
| Bromine content, % by weight | 23.3 | 22.5 |
| Phosphorus content, % by weight | 3.4 | 3.5 |
| Hydroxyl number, mg KOH/g | 40 | 41 |
| Acid number, mg KOH/g | — | <0.3 |
| Mean functionality | 2 | |
| Viscosity at 25° C., Pa.s | — | 4 |
| Specific gravity, g/cm$^3$ | — | 1.30 |

Phosphobrominated polyetherpolyols which are identical in every respect are produced by repeating Example 4 with the total amount of all the reagents introduced at the start.

EXAMPLE 5

Comparative Example 5 illustrates the production of phosphobrominated polyetherpolyols outside the scope of the invention, of general formula (I) in which:

$$Z = -CH_2-\underset{\underset{Br}{|}}{\overset{\overset{Br}{|}}{C}}=C-CH_2-$$

$$Y = -CH_2-\underset{\underset{CH_3}{|}}{CH}-O- \quad \text{and/or} \quad -\underset{\underset{CH_3}{|}}{CH}-CH_2-O-$$

X = —O—CH$_2$—CH$_3$
z = 2             pz = 5
mz = 2.50         pz (n$_1$ + n$_2$) = 12.50 and which possess a ratio $$\frac{\Sigma Y}{\Sigma P}\text{ equal to } \frac{2.50 + 12.50}{5} = 3.$$

These polyetherpolyols are manufactured using a hydroxylated initiator (II) and a brominated polyoxypropylenediol (III) which are identical and which both result from the addition of 2.50 moles of propylene oxide on average to one mole of 2,3-dibromo-2-butene-1,4-diol, phosphorus oxychloride and ethanol.

Using the apparatus of Example 1 and under the general conditions of Example 1, the following are reacted in solution in 1,2-dichloroethane in three successive stages:

(1) 39.1 g (0.1 mole) of brominated polyoxypropylenediol (III) with 76.8 g (0.5 mole) of POCl$_3$ in the presence of 15.8 g (0.2 mole) of pyridine, (2) 195.5 g of brominated polyoxypropylenediol (III) are reacted with the product of the reaction (I) in the presence of 63.3 g of pyridine, (3) 25.3 g (0.55 mole) of ethanol are reacted with the product of the reaction (2) in the presence of 41.5 g (0.525 mole) of pyridine.

After the mixture is washed with water and the volatile materials are removed, a 98% yield is produced of the phosphobrominated polyetherpolyols as defined above, possessing the following characteristics:

|  | Theoretical values | Measured values |
| --- | --- | --- |
| Molecular weight | ±2,800 | |
| Bromine content, % by weight | 34 | 32 |
| Phosphorus content, % by weight | 5.5 | 5.4 |
| Hydroxyl number, mg KOH/g | 40 | 36 |
| Acid number, mg KOH/g | — | <1 |
| Mean functionality | 2 | |
| Viscosity at 25° C., Pa.s | — | 95 |
| Specific gravity, g/cm$^3$ | — | 1.51 |

EXAMPLE 6

Example 6 illustrates the use of phosphobrominated polyetherpolyols obtained in Example 2 in the manufacture of a flame-retardant flexible polyurethane foam.

In an 800-cm$^3$ polyethylene vessel, there are introduced:
180 g of non-halogenated polyetherpolyol TERCAROL 908
20 g of phosphobrominated polyetherpolyol produced in Example 2
6 g of water
1.4 g of silicone
1.0 g of a mixture containing 33% by volume of 1,4-diazabicyclo[2.2.2]octane and 67% of dipropylene glycol marketed under the trade name DABCO 33 LV, and
0.34 g of stannous octoate.

This mixture is stirred for one minute so as to make it completely homogeneous. An 80:20 mixture of toluylene 2,4- and 2,6-diisocyanate (TDI 80/20) having an index of 105 is then added. The resulting mixture is stirred rapidly for 7 seconds and then poured into a box 20×20×20 cm. The cream time and rise time amount, respectively, to 12 and 95 seconds. The foam then undergoes curing for 10 h at 100° C. A cubic block of side 15 cm is cut out and the density is measured, this being 33 kg/m$^3$.

Furthermore, the properties of the foam are measured, and especially the permeability, resilience, compressive strength (load-bearing capacity) according to DIN standard 53,377, rupture strength according to DIN standard 53,571 and elongation at break, permanent deformation according to DIN standard 53,572 (% loss after compression for 22 h at 70° C.) and finally the flame resistance according to MVSS standard 302, before and after ageing.

The ingredients used in the manufacture of the polyurethane foam are recorded in the appended Table I. The properties of the polyurethane foam are recorded in the appended Table II.

EXAMPLES 7 to 10

Examples 7 to 10 are carried out under the general conditions of Example 6.

The ingredients used in the manufacture of the flexible polyurethane foams are recorded in the appended Table I, and the properties of the polyurethane foams are recorded in the appended Table II.

TABLE I

Ingredients used in the manufacture of the flexible polyurethane foams, g

| Ingredients | 6 | 7 | 8 | 9 | 10 |
|---|---|---|---|---|---|
| Non-halogenated polyetherpolyol TERCAROL 908 | 180 | 180 | 180 | 180 | 200 |
| Phosphobrominated polyetherpolyol according to Example 2 | 20 | — | — | — | — |
| Phosphobrominated polyetherpolyol according to Example 1 | — | 20 | — | — | — |
| Phosphobrominated polyetherpolyol according to Comparative Example 5 | — | — | 20 | — | — |
| Phosphochlorinated polyetherpolyol EXOLIT 413 | — | — | — | 20 | — |
| Water | 6 | 6 | 6 | 6 | 6 |
| Silicone | 1.4 | 1.4 | 1.4 | 1.4 | 1.4 |
| 1,4- Diazabicyclo-[2.2.2]octane DABCO 33 LV | 1.0 | 1.0 | 1.0 | 1.0 | 1.0 |
| Stannous octoate | 0.34 | 0.30 | 0.70 | 0.24 | 0.30 |
| TDI 80/20 (index 105) | 75.8 | 76.2 | 75.8 | 78.0 | 75.4 |

TABLE II

Properties of the flexible polyurethane foams

| Properties | 6 | 7 | 8 | 9 | 10 |
|---|---|---|---|---|---|
| Cream time, sec. | 12 | 14 | 14 | 12 | 12 |
| Rise time, sec. | 95 | 100 | 120 | 97 | 102 |
| Density, kg/m$^3$ | 33.6 | 34.1 | 33.4 | 34.1 | 33.3 |
| Permeability, mm water column | 1.1 | 1.1 | 1.1 | 1.1 | 1.1 |
| Resilience, % | 48 | 48 | 47 | 51 | 52 |
| Compressive strength (load-bearing capacity), kPa at compression ratio of | | | | | |
| 25% | 2.50 | 2.55 | 2.40 | 2.35 | 2.60 |
| 40% | 2.80 | 2.80 | 2.65 | 2.65 | 2.90 |
| 60% | 5.20 | 5.60 | 4.95 | 4.90 | 5.60 |
| Rupture strength, kPa | 100 | 110 | 80 | 80 | 100 |
| Elongation at break, % | 197 | 190 | 135 | 140 | 180 |
| Permanent deformation, % at compression ratio of | | | | | |
| 50% | 4 | 4 | 2 | 6 | 2 |
| 75% | 6 | 8 | 6 | 64 | 4 |
| 90% | 6 | 10 | 6 | 85 | 6 |
| Flame resistance, MVSS standard* | | | | | |
| before ageing | SE | SE | SE | SE | BC |
| after ageing for 22 h at 140° C. | SE | SE | SE | SE | BC |

*BC = burns completely
SE = self-extinguishing (distance burnt less than 4 cm)

We claim:

1. A phosphobrominated polyetherpolyol which contains oxyalkylene radicals bound to phosphorus atoms in the phosphate or phosphonate state and 1,4-dioxy-2,3-dibromo-2-butylene radicals in which the ratio of the total number of oxyalkylene radicals to the total number of phosphorus atoms is at least 7, and corresponding to the general formula:

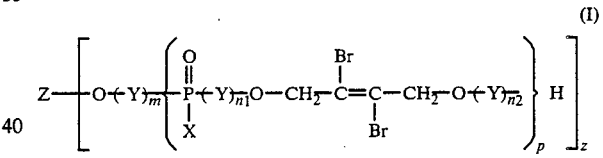

(I)

in which
Z denotes a non-hydroxylated aliphatic radical containing from 1 to 6 carbon atoms and of valence z
Y denotes oxyalkylene radicals derived from ethylene oxide, propylene oxide and/or butylene oxide, the radicals Y derived from ethylene oxide representing at most 50 moles % of all the Y radicals
X denotes monovalent aliphatic radicals, which may be identical or different, chosen from radicals of the —R or —OR type in which R denotes a saturated alkyl radical, optionally halogenated, containing from 1 to 3 carbon atoms, and radicals of the type

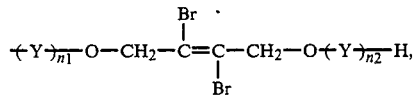

z denotes an integer ranging from 1 to 4
m denotes a number such that $0 \leq zm \leq 50\,z$
p denotes a number such that $z \leq zp \leq 5\,z$ and
$n_1$ and $n_2$ denote numbers other than zero, such that $2\,pz \leq pz\,(n_1+n_2) \leq 12\,pz$, these phosphobrominated polyetherpolyols being further characterized by a ratio of the total number of oxyalkylene radicals to the total number of phosphorus atoms equal to at least 7.

2. Phosphobrominated polyetherpolyols according to claim 1, characterized in that:

Z denotes a non-hydroxylated aliphatic radical containing from 3 to 5 carbon atoms and of valence z Y denotes oxyalkylene radicals derived from propylene oxide X denotes monovalent aliphatic radicals, which may be identical or different, chosen from radicals of the —OR type in which R denotes a halogenated aliphatic radical containing 2 or 3 carbon atoms, the halogen being chosen from chlorine and bromine, and radicals of the type

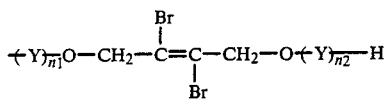

z denotes an integer ranging from 2 to 3 m denotes a number such that $z \leq zm \leq 25\, z$ p denotes a number such that $z \leq zp \leq 3\, z$ and $n_1$ and $n_2$ denote numbers other than zero such that $2\, pz \leq pz\, (n_1+n_2) \leq 10\, pz$.

3. Phosphobrominated polyetherpolyols according to claim 1 to 2, characterized in that the ratio of the total number of oxyalkylene radicals to the total number of phosphorus atoms is between 8 and 12.

4. Process for producing phosphobrominated polyetherpolyols according to claim 1, comprising steps for, condensing in a first stage, z moles of phosphodichlorinated reagent (IV) in the presence of one mole of hydroxylated initiator (II) to produce a phosphochlorinated product (V) and, condensing in a second stage, pz moles of brominated polyoxyalkylenediol (III) and (p−1) z moles of phosphodichlorinated reagent (IV) in the presence of the product (V) resulting from the preceding stage.

5. Process for producing phosphobrominated polyetherpolyols according to claim 1, comprising steps for, condensing in a first stage, z moles of phosphorus oxychloride in the presence of one mole of hydroxylated initiator (II) to produce a phosphodichlorinated product (VI), condensing in a second stage, pz moles of brominated polyoxyalkylenediol (III) and (p−1) z moles of phosphorus oxychloride in the presence of the product (IV) resulting from the preceding stage, to produce a phosphobrominated polyetherpolyol (VII) and, in a third stage, a total of pz moles of saturated aliphatic alcohol, optionally halogenated, containing from 1 to 3 carbon atoms and/or brominated polyoxyalkylenediol (III) are condensed in the presence of the product (VII) resulting from the preceding stage.

6. Process for producing phosphobrominated polyetherpolyols according to claim 4, characterized in that the different condensation stages are carried out in a chlorinated organic solvent, at low temperature, in the presence of an organic basic accelerator chosen from tertiary amines.

7. Process for producing phosphobrominated polyetherpolyols according to claim 4, characterized in that all the phosphochlorinated reagent is introduced at the beginning of the first condensation stage and in that the progress of the successive condensation stages is regulated by the successive addition of appropriate amounts of basic accelerator.

* * * * *